United States Patent [19]

Dumican

[11] Patent Number: 4,923,470

[45] Date of Patent: May 8, 1990

[54] PROSTHETIC TUBULAR ARTICLE MADE WITH FOUR CHEMICALLY DISTINCT FIBERS

[75] Inventor: Barry L. Dumican, Newtown, Conn.

[73] Assignee: American Cyanamid Company, Stamford, Conn.

[21] Appl. No.: 171,606

[22] Filed: Mar. 22, 1988

Related U.S. Application Data

[63] Continuation-in-part of Ser. No. 929,577, Dec. 24, 1986, Pat. No. 4,871,365, which is a continuation of Ser. No. 727,326, Apr. 25, 1985, Pat. No. 4,652,264.

[51] Int. Cl.$^5$ ................................................ A61F 2/02
[52] U.S. Cl. .......................................... 623/11; 623/1; 623/66; 623/13; 606/230
[58] Field of Search ........................ 128/334 R, 335.5; 623/1, 2, 11, 13, 66; 606/230

[56] References Cited

U.S. PATENT DOCUMENTS

| | | | |
|---|---|---|---|
| 3,463,158 | 8/1969 | Schmitt et al. | 128/334 R |
| 3,945,052 | 3/1976 | Liebig | 623/1 |
| 4,137,921 | 2/1979 | Okuzumi et al. | 128/335.5 |
| 4,314,561 | 2/1982 | Kaplan | 128/335.5 |
| 4,517,687 | 5/1985 | Liebig et al. | 623/1 |
| 4,610,688 | 9/1986 | Silvestrini et al. | 623/1 |
| 4,652,264 | 3/1987 | Dumican | 623/1 |
| 4,792,336 | 12/1988 | Hlavacek et al. | 623/13 |
| 4,834,755 | 5/1989 | Silvestrini et al. | 623/13 |

FOREIGN PATENT DOCUMENTS 8800813 2/1988 PCT Int'l Appl. .

Primary Examiner—Randall L. Green
Assistant Examiner—Paul Prebilic
Attorney, Agent, or Firm—Charles F. Costello, Jr.

[57] ABSTRACT

A tubular prosthetic article having at least four chemically distinct fibers is disclosed. A first and second fiber are made of absorbable polymers and a third and fourth fiber are made from nonabsorbable polymers. The absorbable polymers are made from the monomeric units of esters such as glycolic acid, lactic acid, polydioxanone and blends of the same. The nonabsorbable polymers may be made from esters such as polyethylene terephthalate, polybutylene terephthalate, polybutester, or blends of the same. These four chemically distinct fibers may be woven or knitted into a tubular form.

6 Claims, No Drawings

PROSTHETIC TUBULAR ARTICLE MADE WITH FOUR CHEMICALLY DISTINCT FIBERS

BACKGROUND OF THE INVENTION

This invention relates to a tubular article and specifically to a vascular graft containing an absorbable or absorbable/nonabsorbable biomaterial. The use of the vascular graft is for repair of the peripheral vascular system and for coronary bypass.

The absorbable material fosters increased tissue ingrowth into the graft as compared to nonabsorbable grafts. Increased tissue ingrowth leads to greater patency through formation of a vascularized neointima and less tendency to be aneurysmal through formation of a suitable adventitia.

The absorbable material can vary and includes polyglycolic acid (hereafter PGA), and a copolymer comprising glycolic acid ester and trimethylene carbonate linkages, e.g. the copolymer in the MAXON TM (American Cyanamid Company, Wayne, N.J. 07470 U.S.A.) suture.

The nonabsorbable material (which is used as the backbone) can be proprietary materials, e.g. a Hytrel TM (E.I. du Pont and Co., Wilmington, Del., U.S.A.) polymer, such as the polymer in the NOVAFIL TM (American Cyanamid Company, Wayne N.J.) suture. Alternatively, the nonabsorbable material can be more conventional polymers including a polyester, polyamide or polypropylene.

There has been a long felt need in the vascular graft art to develop a small diameter graft which will be generally acceptable to essentially all of the surgical community. The reasons for this long felt need are many and relate both to the biological requirements for a small diameter graft and to the limitations of the biomaterials generally used for these applications. Consequently, prior art small diameter vascular grafts, e.g. at or less than 8 mm diameter to even smaller diameter grafts, e.g. at or less than 4 mm diameter, have not been universally accepted by the surgical community.

Various prior art vascular graft constructions and/or biomaterials have been used in an attempt to solve this long felt need. These prior art solutions have included but are not limited to, one or a combination of the following parameters:

1. Knitted or woven textile structures as vascular grafts for coronary artery bypass and the peripheral vascular system.
2. a. Vascular grafts having a biocomponent structure, i.e. one or more absorbable and nonabsorbable materials.
   b. The percentage of the absorbable material has varied from about 25 to less than 100%.
3. PGA as the absorbable component.
4. A polyester, e.g. Dacron TM (E.I. DuPont & Co., Del., U.S.A.), a polyamide, or a polypropylene as the nonabsorbable component.

None of these prior art solutions have been universally accepted by the surgical community for a small diameter vascular graft. Therefore, the surgical community continues to feel the need for an absorbable or absorbable/nonabsorbable small diameter vascular graft having a diameter of at or less than 8 mm. diameter, and more specifically, at or less than 4 mm. diameter.

To solve this long felt need, critical questions about vascular graft construction and use have to be considered, including, but not limited to, the following:

a. What is the porosity of the vascular graft?
b. What is the compliance of the vascular graft?
c. What are the optimum textile and biological factors for manufacturing a graft, having a double tube configuration specifically, a nonabsorbable outer tube and an absorbable inner tube structure?
d. What are the optimum textile and biological factors for manufacturing a vascular graft having an external support structure?

SUMMARY OF THE INVENTION

A tubular article useful in prosthetic surgery has been invented. The article has a plurality of fibers manufactured from an absorbable polymer. The polymer comprises at least one trimethylene carbonate linkage. In one embodiment, the absorbable polymer is a copolymer. In another embodiment, the article is manufactured on a warp knitting machine. The absorbable polymer comprises more than about 50% by weight of the article. The remainder of the article, if any, comprises a plurality of fibers manufactured from a nonabsorbable polymer.

Another embodiment is an article manufactured on a weft knitting machine. The absorbable polymer comprises more than about 50% by weight of the article. The remainder of the article, if any, comprises a plurality of fibers manufactured from a nonabsorbable polymer.

Yet another embodiment is a woven article. The absorbable polymer in the warp and weft yarns comprises more than about 50% by weight of the article. The remainder, if any, comprises a plurality of fibers manufactured from a nonabsorbable polymer.

A generic embodiment of all of the above is a tubular article comprising a vascular graft.

A vascular graft has also been invented. The vascular graft has a plurality of fibers which are manufactured from an absorbable copolymer. The copolymer comprises up to about 50% by weight of trimethylene carbonate linkages. The copolymer in the MAXON TM (American Cyanamid Company, N.J., U.S.A.) suture contains a copolymer having trimethylene carbonate linkages. MAXON TM, which is a poly(glycolide- co-trimethylene carbonate), has superior and unexpected properties when contrasted to other absorbable fibers. It is long-lasting. A portion of its original strength is retained out to 56 days; 50% of the strength remains through 28 days. The absorption rate of MAXON TM is approximately equal to PGA.

A MAXON TM fiber is more compliant than polyglycolic acid (herein PGA). A graft containing 75% MAXON TM in combination with Dacron TM has a measured compliance of 3.03. A similarly constructed PGA/Dacron TM graft has a compliance of 2.45. Compliance is measured as a percentage of diametral change per 100 mm Hg internal pressure change. Finally, the bending modulus of MAXON TM is approximately 325,000 p.s.i., indicating that MAXON TM is a much more flexible fiber than other absorbable fibers.

In one embodiment, the copolymer comprises about 50% by weight of glycolic acid ester linkages. In another embodiment, the copolymer consists of at least one glycolic or lactic acid ester linkage.

Another embodiment is a graft which is manufactured on a warp knitting machine. The absorbable polymer comprises more than about 50% by weight of the article. The remainder, if any, comprises a plurality of fibers manufactured from a nonabsorbable polymer. In a specific embodiment, the graft is manufactured on a Raschel knitting machine. In another specific embodiment, the plurality of nonabsorbable polymer fibers of the graft comprises about 20 to 35% by weight of the graft. In a more specific embodiment, the plurality of absorbable and nonabsorbable fibers are separately texturized by either a false twist or a knit/deknit process. In a most specific embodiment, the nonabsorbable polymer is Hytrel®. Another most specific embodiment is wherein the nonabsorbable polymer is polyethylene terephthalate.

Hytrel TM is a trademark of E.I. DuPont de Nemours & Co., Wilmington, Del. U.S.A. for a class of polymers having the following generic formula:

hence, has a higher probability of remaining patent in small diameter applications.

(4) Based upon animal studies, a PGA- and MAXON TM containing graft tends to have greater patency than a commercial graft material.

The concentric relationship can be a plurality of single tubes attached together by sewing, gluing, or merely held together by frictional contact between the layers.

The MAXON TM and/or PGA absorbable components of the graft become absorbed and are replaced by natural tissue. This leaves skeletal structure of nonabsorbable Dacron TM or Novafil TM fiber which is encapsulated in healthy collagenous tissue. The inside wall or neointima of the skeletal structure develops into an endothelial-like growth. The outside wall has been shown to be comprised of a matrix of mature, highly vascularized granulation tissue.

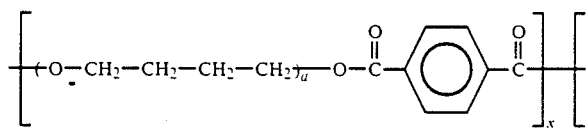

polytetramethylene glycol terephthalate

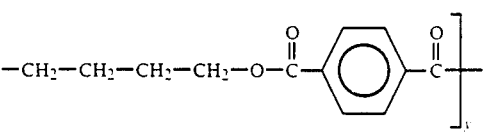

polybutylene terephthalate

The values for a, x and y are known from the prior art, e.g. as disclosed in "Thermoplastic Copolyester Elastomers: New Polymers For Specific End-Use Applications", M. Brown, Rubber Industry 9 102–106 (1978), and the references (footnote numbers 1b, 1c, 1d, 2 and 3) cited therein; Encyclopedia of Polymer Science and Technology, Supplement, 2 485–510, see particularly pages 486 to 493, Interscience N.Y. 1977; and U.S. Pat. No. 4,314,561 issued Feb. 9, 1982. All of this prior art is incorporated herein by reference. A specific embodiment of Hytrel® which is useful in this invention is a grade of Hytrel® having a 72 durometer D hard.

The polymer in the Novafil TM (American Cyanamid Company, N.J., U.S.A.) suture contains Hytrel®. Novafil TM, which is a polybutester, has superior and unexpected properties when contrasted to other nonabsorbable fibers. It is more flexible than other convention-al-type graft fibers, e.g. Dacron TM. Novafil TM has a bending modulus of approximately 230,000 p.s.i. Also, the compliance of a Novafil TM containing graft measures 4.20 in combination with MAXON TM. A similar graft manufactured from Dacron TM and Maxon TM has a compliance of 3.03. Compliance is measured as a percentage of diametral change per 100 mm Hg internal pressure change.

Finally, a tubular article useful in prosthetic surgery and having a plurality of fibers manufactured from a nonabsorbable polymer has been invented. In a specific embodiment, the nonabsorbable polymer is Hytrel®.

A concentric knit relationship, wherein PGA comprises the inner tube, Maxon TM comprises the middle tube, and either Dacron TM or Novafil TM comprises the outer tube, has the following synergistic advantages:

(1) Dacron TM is known from the prior art to incite a thrombogenic reaction.

(2) Dacron TM or Novafil TM fibers can be shielded from blood by inner layers of PGA and MAXON TM, thereby minimizing the tendency to thrombose and occlude the graft.

(3) As PGA and then MAXON TM degrade and are absorbed, the inner capsule becomes larger and, This invention also relates to a nonabsorbable vascular graft manufactured from a Hytrel TM polymer, such as the polymer in the Novafil TM suture.

This invention further relates to the method of texturizing and to the method of using the nonabsorbable vascular graft manufactured from the Hytrel TM polymer and/or the Novafil TM suture. For a description of manufacturing the Hytrel TM polymer, see e.g., U.S. Pat. Nos. 3,766,146; 3,763,109; 3,023,192; and Great Britain Pat. No. 1,458,341; for a description of manufacturing the Novafil TM suture, see, e.g., U.S. Pat. Nos. 4,224,946 and 4,314,561. All of these patents are incorporated herein by reference.

The materials can be constructed into vascular grafts in several ways: (1) as woven single tubes, (2) as warp or weft knit single tubes, (3) as double triple, etc. concentric tubes, and (4) as single wover or knit tubes that are externally supported. The materials can also be constructed from a fabric having a changing composition, e.g. a graded transition section in a fabric or a bicomponent filament. See U.S. Pat. No. 3,463,158 issued Aug. 26, 1969 entitled Polyglycolic Acid Prosthetic Devices, which is incorporated herein by reference. The graft structures can be either straight or bifurcated (branched) tubes.

A knitted tube can be manufactured on a Raschel knitting machine. The number of needles per inch can be about 25 to 35. The gauge (which is twice the number of needles per inch) can therefore be about 50 to 70. Prior art Raschel knitting machines are commercially available in a 56, 60 or 64 gauge.

This invention relates to an improved tubular article. Specifically, this invention relates to a quadricomponent or more tubular article.

The improved tubular article is disclosed in the embodiments, which are:

1. A quadricomponent tubular article useful in prosthetic surgery have a plurality of fibers manufactured from at least two different absorbable and two different nonabsorbable polymers.

2. An article of embodiment 1 wherein at least one of the absorbable polymers is a copolymer.

3. A warp knit article of embodiment 1 wherein the absorbable polymer fibers comprise more than about 50% by weight of the article.

4. A weft knit article of embodiment 1 wherein the absorbable polymer fibers comprise more than about 50% by weight of the article.

5. A woven article of embodiment 1 wherein the absorbable polymer fibers in the warp and weft yarns comprise more than about 50% by weight of the article.

6. An article of embodiment 1 or 2 or 3 or 4 or 5 comprising a vascular graft.

7. A vascular graft having a plurality of fibers manufactured from at least two different absorbable and two different nonabsorbable polymers, at least one of the absorbable polymers being a copolymer, the copolymer comprising up to about 50% by weight of trimethylene carbonate linkages.

8. A graft of embodiment 7 wherein said copolymer comprises about 50% by weight of glycolic acid ester linkages.

9. A graft of embodiment 7 wherein said copolymer consists of at least one glycolic or lactic acid ester linkage.

10. A warp knit graft of embodiment 8 wherein the absorbable polymer fibers comprise more than about 50% by weight of the graft.

11. A Raschel knit graft of embodiment 10.

12. A graft of embodiment 7 or 8 or 9 or 10 or 11 wherein the plurality of nonabsorbable polymer fibers comprises about 20 to 35% by weight of the graft.

13. A graft of embodiment 12 wherein the plurality of absorbable and nonabsorbable fibers are separately texturized by either a false twist or a knit/deknit process.

14. A graft of embodiment 12 wherein at least one of the nonabsorbable polymers is selected from the group consisting of a poly($C_2$-$C_{10}$ alkylene terephthalate), poly($C_2$)-$C_6$ alkylene), polyamide, polyurethane, and polybutester.

15. A graft of embodiment 12 wherein one of the nonabsorbable polymers is polyethylene terephthalate.

16. A graft of embodiment 12 wherein one of the nonabsorbable polymers is polybutylene terephthalate.

17. A graft of embodiment 12 wherein one of the nonabsorbable polymers is a spandex polymer.

18. A graft of embodiment 12 wherein one of the nonabsorbable polymers is a polybutester.

19. A graft of embodiment 14 wherein the nonabsorbable polymers are polyethylene terephthalate and a spandex polymer.

20. A tubular article useful in prosthetic surgery having a plurality of at least three different fibers, the first and second fibers manufactured from two different absorbable polymers, and the third fiber manufactured from a nonabsorbable polymer, the improvement comprising a fourth fiber, the third and fourth fibers manufactured from two different nonabsorbable polymers.

21. A knitted vascular graft having a plurality of at least three different fibers, the first and second fibers manufactured from two different absorbable polymers, one of said polymers comprising up to about fifty percent by weight of trimethylene carbonate linkages, and the third fiber manufactured from a nonabsorbable polymer, the improvement comprising a fourth fiber, the third and fourth fibers manufactured from two different nonabsorbable polymers.

22. A vascular graft having at least three different components, said first, second and third components manufactured respectively from three different fibers, the first and second fibers manufactured from two different absorbable polymers, one of said polymers comprising up to about fifty percent by weight of trimethylene carbonate linkages, and the third fiber manufactured from a nonabsorbable polymer, said components knitted or woven together in a concentric relationship, the improvement comprising a fourth fiber, the third and fourth fibers manufactured from two different nonabsorbable polymers.

23. An article of embodiment 1 or 3 or 7 or 14 or 19 or 20 comprising an external support, said support having at least one fiber, said fiber helically wrapped and attached to said article.

24. A tubular article of embodiment 20 useful in prosthetic surgery having a plurality of third fibers manufactured from a nonabsorbable polymer, said polymer comprising a polybutester.

25. An article of embodiment 20 or 21 or 22 wherein at least one of the absorbable polymers is selected from the group consisting of poly(glycolic acid), poly(lactic acid), polydioxanone, and blends of the same.

26. An article of embodiment 25 wherein the poly(glycolic acid) is a homopolymer.

27. An article of embodiment 25 wherein the poly(glycolic acid) is a copolymer.

28. An article of embodiment 27 wherein the copolymer is manufactured from the monomer glycolic acid and from one or more non monomers selected from the group consisting of lactic acid, trimethylene carbonate and $\epsilon$-caprolactone.

29. An article of embodiment 20 or 21 or 22 wherein the first fiber is manufactured from a copolymer of glycolic acid and trimethylene carbonate; the second fiber is manufactured from a homopolymer of glycolic acid; the third fiber is manufactured from a polymer selected from the group consisting of polyethylene terephthalate, polybutylene terephthalate, a polybutester, and blends of the same; and the fourth fiber is manufactured from a spandex polymer.

30. An article of embodiment 34 wherein the first fiber comprises about 35 to 55%; the second fiber comprises about 15 to 35%; the third fiber comprises about 10 to 20% of polyethylene terephthalate; and the fourth fiber comprises about 5 to 15%, all percentages based on the total weight of the article.

31. An article of embodiment 2 wherein the first, second and third fibers are separately texturized by either a false twist or a knit/deknit process.

It is to be understood that the embodiment can be amended without adding or subtracting from the scope of this invention.

A drawing which describes the shape and/or geometrical configuration of the improved tubular article is not necessary for an understanding of this invention. That is, any person skilled in vascular graft art will know how to manufacture and how to use the invention by reading this specification, generally and the examples 7 to 18, specifically.

Throughout this disclosure, it is to be understood that the term Lycra is a trademark of the E.I. DuPont and Company, DE, U.S.A., whether the term Lycra is or is not so identified as a trademark.

The term polyurethane is generic and includes both the polyether and polyester types. A polyether type spandex is preferred. The Lycra ™ described in the examples 7 to 18 is a polyether type polyurethane.

It is to be understood that the term polybutester as used in this disclosure is synonymous with the terms polyetherester, polyether-ester or polyether ester. A commercially available polybutester is the Hytrel ™ (E.I. DuPont and Co.) copolymer.

The external support described in embodiment 23 can be attached to the tubular article, e.g. a vascular graft, by either melt or adhesive attachment.

DESCRIPTION OF THE PREFERRED EMBODIMENT

The following steps are followed when preparing knit vascular grafts starting from the appropriate yarns. The proper denier yarns for the specific construction have to be knit. If the denier to be used can only be obtained by using three or more ends, the yarn must be ply-twisted together. For example, if the construction is a 330-denier PGA and 100-denier textured Dacron ™, and the only available PGA is 110-denier, it is necessary to twist three ends of 110-denier PGA and the one end of 100-denier Dacron ™. Other variations can be used, depending on the type of construction called for. After ply-twisting onto a king spool, the twisted yarn is transferred to a model 50 cone, using a coning machine. It is preferred that any material that is not twisted and is to be used for knitting be transferred to a cone, or to a similar type package from which the yarn may easily be removed. The yarn is then set up on the knitting machine.

The knitting machine can be commercially available. It can be a floor-type self-contained unit, completely assembled, with exception of the yarn tension or stop-motion assembly. A direct V-belt drive from a fractional horsepower motor to the knitting head allows for a quiet knitting speed up to about 1100 r.p.m. A variable speed take-down assures minimum breakdowns and absolute quality stitch control. Operating speeds can vary depending on cylinder size and also the type of yarn or fibers used.

The proper density of the graft construction is obtained by changing the stitch cam and take-down settings. The stitch cam controls the length of the stitch, and the take-down controls the tension of the tubular fabric being knit.

After knitting, the graft material is scoured in xylene under ultrasonic agitation for two ten-minute baths. The material is allowed to dry in a fume hood until no xylene odors can be detected. The graft material is then cut to appropriate lengths (e.g. 4 mm×60 mm; and/or 8 mm×80 mm) and then reversed.

Reversing involves turning the graft inside out to have a smooth inner surface, and a rougher outer surface to promote ingrowth. Any graft containing PGA is then post-treated on stainless steel mandrels at temperatures of about 115° C. to 150° C., under a vacuum approximately equal to 1 torr or lower. The post-treatment process seems to increase the tensile strength retention for the absorbable component, up to about 60 days after implant. A graft that does not contain PGA may not undergo the post-treatment process.

The ends of the graft may then be heat-sealed on a hot surface to prevent unravelling. During heat-sealing, the ends of the graft are melted only slightly.

Following scouring in xylene or another medically approved nonaqueous solvent and drying, the graft is then packaged in a polycarbonate folding container, which is then placed in a foil inner pouch. The graft is then sent through an absorbable device EtO-sterilization cycle. After sterilization, the graft is repacked in a 2-web TYVEK ® (a spun bonded polyolefin manufactured by E.I. DuPont & Co., Wilmington, Del., U.S.A.)/Mylar ™ (a polyethylene terephthalate also manufactured by E.I. DuPont & Co.) pouch, sealed and EtO-sterilized a second time.

A series of in vivo studies with woven vascular grafts in several configurations was completed. The following materials, although not exclusive, were included:
  (a) PGA/Dacron ™ 80/20 low and high porosity, 4 and 6 mm in diameter
  (b) PGA/copolymer having glycolic acid ester, and trimethylene carbonate linkages, 4 mm
  (c) Woven non-crimped Dacron ™, 4 and 6 mm; and
  (d) Gore-Tex (a Trademark of Wil-Gore & Associates, Inc.) 4, 8 and 10 mm.

The overall patency rate for PGA containing grafts was substantially higher than controls: 58% vs. 41%.

Bi- and tri-component vascular grafts made of biodegradable and non-degradable fibers have been studied in the beagle. Observations carried out from ~30 days to ~7 months showed that as the absorbable component left the graft structure, organized and oriented tissue invaded the graft approximating the location of the degraded material. The tissue ingrowth appeared to mobilize as a neointima with the lumenal surface covered by cells strongly resembling endothelium. The non-degradable component exhibited dispersed fibers within a matrix of mature, highly vascularized granulation tissue. This rich blood supply persisted for the period of maximum observation.

The graft structures were provided in two diameters: 4 and 8 mm ID. The former were studied as interpositional grafts in both carotids of the host; the latter as interpositional grafts in the thoracic aorta. The 4 mm grafts (40–60 mm in length) were examined at 1 and 2 months and showed high degrees of patency. The tissue reaction showed progressively increasing tissue incorporation although endothelization was absent at 1 month and only partially manifest at 2 months. The 8 mm grafts examined at ~3–~7 months were uniformly patent and showed uninterrupted complete endothelization of the graft lumen and complete replacement of the degradable material by the tissue elements noted above.

The present invention is illustrated by the following examples which can be useful in peripheral vascular surgery, as coronary artery bypasses or in general arterial or venous grafting.

EXAMPLE 1

This graft is a double-walled structure consisting of a 100% PGA woven inner tube and a 100% texturized knit Dacron ™ velour outer tube. The structure was designed so that the inner wall, being PGA, would become absorbed and be replaced by a smooth, well-organized tissue at least partially consisting of endothelial cells. This inner wall would become the new intima. The outer wall, being constructed of porous nonabsorbable Dacron ™ material, would allow tissue and capillary ingrowth and, at the same time, add support to the newly-grown neointima to prevent aneurysms. The Dacron ™ outer wall material is a Sauvage Filamentous Velour ® fabric supplied by U.S.C.I., a division of C.R. Bard Co., Inc., Billerica, Mass., U.S.A. The inner wall fabric is a woven tube having a 1×1 plain weave construction using 5-ply, 46-denier, 21 filament (PGA) polyglycolic acid yarn in both the warp and filling direction.

The graft materials were scoured in xylene in an ultrasonic bath—2 baths of fresh xylene for 10 minutes each—to remove fiber spin finish.

The outer and inner tubes for the 4 mm I.D. grafts were cut to approximately 45 mm in length. The tubular woven PGA material was mounted on stainless steel rods, placed in a vacuum chamber and treated at 130° C. for 3 hours under a vacuum of less than 1 torr (a similar treatment was done for the 8 mm tubes, except they were cut to 80 mm length).

Next, the inner and outer tubes were stitched together by placing either 3 (4 mm I.D.) or 4 (8 mm I.D.) longitudinal rows of stitches between inner and outer wall. The double tube grafts were then packaged and EtO-sterilized prior to use as implants.

Following graft construction and sterilization, the 4 mm grafts were implanted in the left and right carotid arteries of thoroughbred beagle dogs. The 8 mm I.D. grafts were implanted in the thoracic aorta. The grafts were left in the animal for periods of up to 90 days, at which time the dogs were sacrificed, and the grafts were dissected and removed for subjective and histological examination.

Examination of the implant sites revealed absorption of the PGA fiber and replacement with a smooth, glistening endothelial-like neointima. The Dacron TM outer wall was ingrown with tissue and small blood vessels. There was little, if any, indication of aneurysmal dilation. Exclusive of technical error during implant, grafts were patent and blood flow, as determined by Doppler recordings, was satisfactory.

EXAMPLE 2

A 3-ply yarn, consisting of 110-denier/50-filament PGA, 105-denier/25-filament MAXON TM (a copolymer having glycolic acid ester and trimethylene carbonate linkages, e.g. as described in U.S. Pat. No. 4,429,080 issued Jan. 31, 1984 and incorporated herein by reference), and 100-denier texturized Dacron TM, was plied together at approximately 2 turns per inch of twist and knit into (a) 4 mm and (b) 8 mm inside diameter (I.D.) tubes. The knitting machine used was a Lamb ST3A circular weft knitting machine. The needle cylinder used had 25 needles per inch of circumference.

Following knitting, the tubular graft material was scoured, cut, post-treated, packaged and sterilized as described in Example 1.

The tricomponent structure, being comprised of both MAXON TM (glycolide-TMC) and polyglycolic acid yarns, after post-treatment attains a tighter, more pebbly velour-like appearance, due to the differential shrinkage between the two absorbable fibers in the presence of textured Dacron TM.

The 4 mm and 8 mm grafts were implanted in beagle dogs, as described under Example 1.

Examination of the implant sites following sacrifice revealed partial to complete absorption of the bioabsorbable yarns, excellent patency, no noticeable aneurysmal formation and a uniform granular tissue forming the neointima and extending through the wall to the advential surface.

Table 1 is a summary of the in vivo animal data for the knit grafts constructed according to Example 2.

TABLE 1

| | | SUMMARY OF ANIMAL DATA ON KNIT GRAFTS | | | | |
|---|---|---|---|---|---|---|
| Graft Composition | Number Implanted | Implant Site | Number Patent | Aneurysmal Tendency 0123[a] | Number Occluded | Number Unsacrificed |
| 33/33/33 PGA/ | 6 | Thoracic Aorta | 5 | 0041 | — | 1 |
| MAXON TM/Textured | 4 | Left Carotid Artery | 3 | 2010 | 1 | — |
| DACRON ® | 6 | Right Carotid Artery | 3 | 0031 | 2 | 1 |

(a) Rating:
0 = None
1 = Possible
2 = Slight
3 = Significant

EXAMPLE 3

A 4-ply yarn consisting of three ends of 105-denier MAXON TM (as described in the Background and in Example 2, above) and one end of 100-denier texturized Dacron TM was plied together at a twist level of approximately 2 turns/inch. The yarn was knit into 4 and 8 mm I.D. tubes on separate Lamb ST3A circular weft knitting machines, using 25-needle per inch knitting cylinders. These grafts had wall thicknesses of between 650 and 850 microns.

Following knitting, the graft material was scoured, cut to 45 and 80 mm lengths, heat-set at 110° C. for 1 to 3 minutes on stainless steel sizing rods, helically wrapped with 2-0 monofilament MAXON TM suture material as a means of external support, packaged and sterilized.

The external support material was attached to the outside surface of the vascular graft, using polymeric glycolide/trimethylene carbonate (TMC) dissolved in methylene chloride as an adhesive. Alternatively, poly-TMC dissolved in methylene chloride can be used as an adhesive. Table 2 is a summary of the in vivo animal data for the knit grafts constructed according to Example 3.

TABLE 2

| | | SUMMARY OF ANIMAL DATA ON KNIT GRAFTS | | | | |
|---|---|---|---|---|---|---|
| Graft Composition | Number Implanted | Implant Site | Number Patent | Aneurysmal Tendency 0123[a] | Number Occluded | Number Unsacrificed |
| 75/25 MAXON TM/ | 6 | Thoracic Aorta | 6 | 2022 | — | — |
| Textured DACRON ® | 3 | Left Carotid Artery | 2 | 1010 | 1 | — |
| with External | 4 | Right Carotid Artery | 4 | 0112 | — | — |

TABLE 2-continued

SUMMARY OF ANIMAL DATA ON KNIT GRAFTS

| Graft Composition | Number Implanted | Implant Site | Number Patent | Aneurysmal Tendency 0123[a] | Number Occluded | Number Unsacrificed |
|---|---|---|---|---|---|---|
| Support* | | | | | | |

(a) Rating:
0 = None
1 = Possible
2 = Slight
3 = Significant

*External support of monofilament MAXON absorbable suture material.

EXAMPLE 4

A 4-ply yarn consisting of two ends of 46-denier PGA, one end of 62-denier PGA and one end of 100-denier texturized NOVAFIL ® was assembled at approximately 2 turns per inch of twist. The texturized NOVAFIL ® yarn was false-twist texturized, using the Helanca ® (trademark of Heberlein Corp., Wattwil, Switzerland) process in order to provide a surface texture that would encourage maximum tissue ingrowth. The combined yarn was knit into 4 and 8 mm I.D. tubes similar to Example 3, except that the cylinder had a needle spacing of 33 needles per inch.

Following knitting, the graft materials were scoured, cut to 45 and 80 mm length tubes, post-treated on stainless steel rods under vacuum of 1 torr at 130° C. for 3 hours, cooled, helically wrapped with 3-0 MAXON TM monofilament suture material, attached to the surface of the graft using poly-TMC as an adhesive and, finally, packaged and sterilized.

EXAMPLE 5

In this warp knit example, 70-denier texturized Dacron TM was combined with 105-denier MAXON TM multifilament yarn on a 48-gauge Raschel knitting machine in the following construction:

| Front Bar | 2/0 | 2/4 | 70-denier textured Dacron TM |
|---|---|---|---|
| Back Bar | 2/0 | 4/6 | 105-denier MAXON TM |

EXAMPLE 6

This construction is similar to Example 5, except that the stitch construction is reversed as follows:

| Front Bar | 2/0 | 4/6 | 105-denier MAXON TM |
|---|---|---|---|
| Back Bar | 2/0 | 2/4 | 70-denier textured Dacron TM |

Examples 5 and 6, although formed on a 48-gauge Raschel machine can be made on a 56-, 60- or 64-gauge Raschel machine, having 14 or more guide bars, positive feeds and stitch combs.

EXAMPLE 7

Two 3-plied yarns each comprised of 50 denier MAXON ® 46 denier PGA and 20 denier textured DACRON ® twisted at 2.3 turns per inch 'Z' twist were fed separately to a Lamb ST-3A circular knitter along with one end of 70 denier LYCRA ® T-126C. The yarns were knit on a 25 needle per inch cylinder in a single jersey stitch to form (1) a 4 mm I.D. and (2) an 8 mm I.D. tube, the wall thickness of which was between 0.60 and 0.70 mm.

Following knitting, the graft material was scoured in xylene, cut to length, reversed and post treated in a vacuum oven at 130° C.±5° C. for $2\frac{1}{2}\pm\frac{1}{2}$ hours.

These grafts were evaluated in dogs in both the carotid artery and thoracic aorta. The results revealed 11 of 12 grafts to be patent with little or no dilation and good tissue ingrowth after sacrifice time periods of 1 and 2 months.

EXAMPLE 8

A graft was made and processed as in Example 7 but using 25 denier textured NOVAFIL ® in place of DACRON ®.

EXAMPLE 9

A graft was made and processed as in Example 7 but using a 33 needle/inch cylinder and the following supply yarns: (1) 3-ply yarn containing 25 denier MAXON ® 26 denier PGA and 30 denier textured DACRON ® twisted at 1.8 turns per inch "S" twist (2) 3-ply yarn containing 2 ends of 25 denier MAXON ® and 1 end of 20 denier PGA twisted at 1.8 T.P.I. "S" and (3) 1 end of 40 denier LYCRA ® T-146C. The wall thickness of the graft was 0.40-0.50 mm.

EXAMPLE 10

A graft as in Example 9 but using 25 denier textured NOVAFIL ® to replace the 30 denier textured DACRON ®.

EXAMPLE 11

A graft construction was made on a 60 gauge (30 needle/inch) double needle bar Raschel warp knitting machine by supplying the following yarns to the inside guide bars (bars 2+7): a 3-ply yarn consisting of 80 denier textured MAXON ® 62 denier textured PGA and 30 denier textured DACRON ®, plied together at 4 turns/inch 'Z' twist and the following yarns to the outside guide bars (bars 1+8): 40 denier T-146C LYCRA ®.

The grafts were knit using the following construction:
Outside Guide Bars (1+8) 2-4/2-0
Inside Guide Bars (2+7) 2-0/2-4

Following knitting, the grafts were processed as in Example 1.

EXAMPLE 12

A graft was made as in Example 11 except that 46 denier textured PGA was used to replace the 62 denier textured PGA.

EXAMPLE 13

A graft was made as in Example 11 except that 25 denier textured NOVAFIL ® was used to replace 30 denier textured DACRON ®.

EXAMPLE 14

A graft was made as in Example 12 except that 25 denier textured NOVAFIL ® was used to replace 30 denier textured DACRON ®.

EXAMPLE 15

A graft was made as in Example 11 except that the knit construction was as follows:
  Outside Guide Bars (1+8) 4-6/2-0
  Inside Guide Bars (2+7) 2-0/2/4

EXAMPLE 16

A graft was made as in Example 15 except that 46 denier textured PGA was used to replace 62 denier textured PGA.

EXAMPLE 17

A graft was made as in Example 15 except that 25 denier textured NOVAFIL ® was used to replace 30 denier textured DACRON ®.

EXAMPLE 18

A graft was made as in Example 16 except that 25 denier textured NOVAFIL ® was used to replace 30 denier textured DACRON ®.

I claim:

1. A tubular article useful in prosthetic surgery having a plurality of at least three different fibers, a first and a second fiber manufactured from two chemically distinct absorbable polymers, and a third fiber manufactured from a nonabsorbable polymer, the improvement comprising at least one of the first or second absorbable polymers being selected from the group consisting of a copolymer of glycolic acid, poly(lactic acid), polydioxanone, and blends of the same, and a fourth fiber, the third and fourth fibers being chemically distinct and manufactured from two different nonabsorbable polymers.

2. A tubular article useful in prosthetic surgery having a plurality of at least three different fibers, a first and a second fiber manufactured from two different absorbable polymers, and a third fiber manufactured from a nonabsorbable polymer, the improvement comprising the first fiber manufactured from a copolymer of glycolic acid and trimethylene carbonate; the second fiber manufactured from a homopolymer of glycolic acid; the third fiber manufactured from a polymer selected from the group consisting of polyethylene terephthalate, polybutylene terephthalate, a polybutester, and blends of the same; and a fourth fiber manufactured from a spandex polymer.

3. The tubular article of claim 1 or 2 wherein one of the absorbable polymers comprises up to about fifty percent by weight of trimethylene carbonate linkages.

4. The tubular article of claim 1 or 2 wherein the fibers are knitted or woven together in a concentric relationship.

5. The tubular article of claim 2 wherein the first fiber comprises about 35 to 55%; the second fiber comprises about 15 to 35%; the third fiber comprises about 10 to 20% of polyethylene terephthalate; and the fourth fiber comprises about 5 to 15%, all percentages based on the total weight of the article.

6. The tubular article of claim 2 wherein the first, second and third fibers are each texturized by either a false twist or a knit/deknit process.

* * * * *